United States Patent [19]
Steer

[11] Patent Number: 5,976,118
[45] Date of Patent: Nov. 2, 1999

[54] WATER—CLOSET DISPOSABLE POUCH

[75] Inventor: Graham E. Steer, Wimbledon, United Kingdom

[73] Assignee: Bristol-Myers Squibb Company, New York, N.Y.

[21] Appl. No.: 08/881,006

[22] Filed: Jun. 23, 1997

[30] Foreign Application Priority Data

Jun. 26, 1996 [GB] United Kingdom .................... 9613360
Jan. 24, 1997 [GB] United Kingdom .................... 9701485

[51] Int. Cl.$^6$ ....................................................... A61F 5/44
[52] U.S. Cl. ........................................... 604/332; 604/333
[58] Field of Search ..................................... 604/332–345

[56] References Cited

U.S. PATENT DOCUMENTS

4,930,942  6/1990  Keyes et al. ............................... 406/49
5,167,650  12/1992  Johnsen et al. .......................... 604/332

*Primary Examiner*—John G. Weiss
*Assistant Examiner*—Dennis Ruhl
*Attorney, Agent, or Firm*—Stuart E. Krieger

[57] ABSTRACT

A water-closet disposable pouch (8) has a pull-away tab (20) secured to one wall (10) by a weld or bond (22). Pulling away the tab (20) tears open the pouch wall (10) along the weld or bond by tearing out material (30) from the weld, thus creating one or more gaps (28). The tab (20) may be V-shaped, and define a flap or hatch area (26) of the wall behind the tab (20) which is released when the tab (20) is torn away. Any gas trapped in the pouch can escape through the opening when the gas is placed in a WC. In an alternative form, a tear-out filament is secured to or within a wall of the pouch parallel to a direction of orientation of the plastics material.

15 Claims, 10 Drawing Sheets

WATER—CLOSET DISPOSABLE POUCH

BACKGROUND OF THE INVENTION

This invention relates to a water-closet (WC) disposable pouch.

As is well known, there have been continuing efforts to design a satisfactory WC-disposable pouch. Such pouches are worn by those who have suffered a surgical diversion operation such as a colostomy. One example of such a pouch is shown in European Patent Application No. 10171B (H. Kiefer), and others in GB 2 083 762B, GB 2 227 668 and GB 2 227 937. EP 272,816 discloses a pouch which has an integral tear strip embedded in its front or rear panel laminate. Despite a variety of approaches, no known pouch design has consistently met the requirements of easy manipulation and consistent WC-flushability. One intractable problem is that air trapped in the pouch causes it to fail to pass around the U-bend of a conventional water-closet.

The present invention has been devised bearing the above problems in mind.

SUMMARY OF THE INVENTION

According to one aspect of the present invention, there is provided a WC-disposable pouch comprising walls of plastics material welded together along at least one edge, a first of the walls having a pull-away element secured to the exterior thereof by one or more plastics welds or bonds such that in use, the pouch wall can be torn open adjacent or along the weld or bond by pulling the element away.

According to another aspect of the invention, there is provided a method of disposing of a pouch for containing body wastes down a WC, a wall of the pouch having thereon a pull away element secured thereto by one or more plastics welds or bonds, the method including pulling the element away to produce a tear adjacent or along the weld or bond, then placing the pouch in the WC to be flushed away.

In a yet further aspect, the invention provides a method for use in the production of a tear-open WC-disposable pouch, comprising providing a sheet of plastics material for forming at least one wall of the pouch, and welding or bonding to a face of the sheet a pull-away element such that the sheet can be torn open adjacent or along the weld or bond by pulling the element away.

Preferably, the element is of plastics material.

Thus, these aspects of the invention can provide an extremely user-friendly technique for tearing open a pouch, to release any trapped air or other gases prior to disposal. The manufacturing of the pouches can also be extremely straightforward, and can avoid any need to embed filaments within the laminate structure of the wall material.

Preferably, when the element (e.g. a tab) is pulled away, it tears out the portion of the wall material which is welded or bonded to the tab itself. In other words, the portion of the wall material welded or bonded to the tab remains attached to the tab, thereby creating a gap between spaced-apart edges of the material wall. The production of a gap in this way avoids any tendency of the wall to re-seal itself when wet, because the torn edges of the plastics material are spaced apart, and are unlikely to come into edge-to-edge contact.

The term "bond" as used herein covers any kind of attachment of the tab or other element to the wall material through the use of an intermediate. For example, the intermediate may be an adhesive, or a hot melt layer. Preferably, the bond strength between the tab and the wall of the pouch is greater than the tear resistance of the wall material, to achieve the desired tear action on pulling away the tab. Preferably, the bond strength is sufficient that the region of the wall bonded to the tab is torn out of the wall, and remains attached to the tab, as described above.

In a particularly preferred form the tab (or other element) is secured to the wall of the pouch by a plastics weld. The weld may be a heat weld or an RF weld. This is advantageous because the welding process is believed to create a line or region of weakness adjacent to the position of the weld. Such a line or region of weakness will be present in both the pull-away tab and the pouch wall. However, the arrangement can be engineered to ensure that the material of the pouch wall tears before the tab itself begins to tear. One way of achieving this is to arrange for the material of the tab to be stronger (at least in the direction of the tear) than the material of the pouch wall. For example, two different materials of different strengths may be used, the relatively weak material being for the pouch wall, and the relatively strong material being for the tab. Additionally, or alternatively (particularly if the same material is used for both the tab and the pouch wall), the tab may be thicker than the pouch wall to provide a greater relative strength.

The welding operation creates what is known as a heat affected zone (HAZ) in the material, in which the structure of the material is believed to be modified by the application of heat sufficient to fuse the material. The line or region of weakness is observed to extend along the periphery of the HAZ, parallel to the weld. It is believed that the weakness may result from local orientation of the polymer chains parallel to the periphery of the HAZ, which would create reduced resistance to tearing. In any event, it has been observed that the material may readily be torn on either side of the weld, the tear(s) extending in a line closely adjacent to the weld, and parallel with the line of the weld.

A similar effect is known to occur in welded metal joints. A metal structure may be vulnerable to shearing in a region adjacent to, but not exactly at, the positions of the welds. This is believed to result from the creation of a HAZ in the metal structure, around the periphery of which the material seems to be weakened.

In addition to the creation of a HAZ in the plastics materials being welded in the present invention, the welding operation also involves pressing the welded materials together to achieve a good weld. This pressing action in combination with the melting of the plastics material to achieve the weld, results in material being thinned (typically by 10–30%), which also reduces the resistance to tearing.

The term "weld" used herein is intended to cover any securing together of the materials by fusion.

The material of the pouch wall (and/or the tab) may be non-orientated, or it may be mono-axially or bi-axially orientated. In one preferred embodiment in which a tab is welded to the pouch wall along to convergent lines, non-orientated plastics material is used, and the tearing open of the pouch relies on the lines of weakness created on either side of each weld line.

In the above aspects of the invention, the weld or bond preferably defines a flap or hatch area of the pouch wall around which the weld or bond extends or at least partially extends and, in use, tearing of the pouch wall by pulling away the tab (or other element) releases the flap or hatch area of the pouch wall from the surrounding material.

The flap or hatch area is preferably an integral part of the pouch wall which behaves as a flap or hatch area of material when surrounding material is torn away by pulling on the pull away element.

With such an arrangement, a large opening can be formed in the pouch wall, by tearing around the hatch or flap area. A hatch area would be completely torn around its periphery so that the hatch material is substantially completely separated from the remainder of the pouch wall. A flap area would be torn partly around its periphery leaving intact a hinge region about which the flap material is free to fold open, to create the opening.

Preferably, the pull-away tab (or other element) has a free edge by which the tab can be grasped to pull it away from the pouch. The free edge may then overlie a region of the pouch wall corresponding to the "hinge" region of the flap.

In a preferred form, the weld or bond lines define a generally V-shaped flap area of the pouch wall. More preferably, the V-shape flap extends substantially from one edge of the pouch to substantially the opposite edge.

In a further, closely related, aspect the invention provides a WC-disposable pouch comprising walls of plastics material welded together along at least one edge, a first of the walls having a pull-away element of plastics material welded or bonded thereto, the weld or bond defining a flap or hatch area of the pouch wall around which the weld or bond extends or at least partially extends and, in use, pulling away of the element releases the flap or hatch area of the pouch wall from the surrounding material.

In a yet further related aspect, the invention provides a WC-disposable pouch comprising walls of plastics material welded together along at least one edge, a first of the walls having a flap or hatch area defined therein by a line or region of weakness extending around or partially around said area in the wall material, and the pouch further comprising a release element attached to or embedded in the wall for breaking the material along the line or region of weakness when the element is pulled, thereby to release the hatch or flap area of material from the surrounding material.

In a yet further, closely related aspect, the invention provides a WC-disposable pouch comprising walls of plastics material welded together along at least one edge, a first of the walls having a pull-away element of plastics material secured to the exterior thereof by generally linear first and second regions of plastics welds or bonds extending opposite each other in a parallel or non-parallel arrangement. Preferably, the first and second regions correspond to opposite edges of the pull-away element. Preferably, the first and second regions are joined together, either directly at a common intersection region, or by a third weld or bond region. Most preferably, the first and second regions form, or form part of, a continuous weld or bond (for example defining a V, U or similar shape).

Referring to the following description of preferred embodiments, when a tab is attached to a pouch wall and a weld is made, so producing a HAZ, pulling on the tab normally results in two tears starting. By a further pull, usually in a downward direction if the pouch is being worn at that time, the tab may be torn completely away, so leaving two tears, e.g. of about 80 to 150 mm. in length in the pouch wall. As a result, a through tear occurs and a part of the pouch wall is torn away.

In use, once the pouch has been filled or part-filled, and the wearer wishes to dispose of it, he or she holds it over the WC and pulls the tab, thus tearing the wall of the pouch. The pouch is then simply dropped into the WC. In effect, by pulling the tab, a thin strip of pouch wall along the length of each of the two sides of the tab is torn away still attached to the tab, so making a pair of longitudinal tears in the pouch wall. The tab preferably extends vertically on the pouch, but may extend in any desired direction.

According to another aspect of the present invention, there is provided a WC-disposable pouch comprising walls of plastics material welded together along at least one peripheral edge, characterised in that one of the walls is made of a linearly-oriented plastics material and has a pull-away tear strip extending in a substantially straight line from one pouch edge to an opposite pouch edge and parallel to the direction of orientation of the plastics material of the wall, whereby the pouch can be torn open.

According to a closely related aspect of the invention, there is provided a method of disposing of a pouch for containing body wastes down a WC, at least one wall of the pouch being made of a linearly-oriented plastics material and having embedded therein a pull-away tear strip extending substantially parallel to the direction of linear orientation of the plastics material of the wall from one pouch edge to the other, in which the pouch is disposed of by pulling end of the ear strip to effect a tear, then placing the pouch in the WC, and flushing the WC.

Alternatively, both of the pouch walls may be made of a linearly-oriented plastics material. The direction of orientation is preferably substantially vertical, assuming the pouch is in a normal, as worn, upright position.

According to a further aspect of the invention, there is provided a WC-disposable pouch comprising walls of plastics material welded together along at least one peripheral edge, wherein a pull-away tear strip is secured to or embedded within a first of the walls along or closely adjacent to an elongate heat affected zone (HAZ) in the wall distinct from the welded periphery.

According to yet a further aspect of the invention, there is provided a method of disposing of a pouch for containing body wastes down a WC, at least one wall of the pouch having a pull-away tear strip embedded in or secured to a first wall along or closely adjacent to an elongate heat-affected zone in the wall distinct from the welded periphery, the method wherein the pouch is disposed of by pulling an end of the tear strip to effect a tear, then placing the pouch in the WC, and flushing the WC.

In use, once the pouch of any of the above aspects has been filled or part-filled, and the wearer wishes to dispose of it, he or she holds it over the WC and pulls a tab connected to the tear strip, thus slitting the wall of the pouch from one edge to the other. The pouch is then simply dropped into the WC. In effect, the pouch is "unzipped" by pulling the tear strip. Preferably the pouch is approximately rectangular or pear-shaped and its said one wall may but need not be linearly oriented in a vertical direction when the pouch is in its usual position when worn. The tear strip also preferably extends vertically, but may extend in any desired direction.

BRIEF DESCRIPTION OF THE DRAWINGS

The invention will be better understood from the following non-limiting description of examples thereof given with reference to the accompanying drawings in which like parts are denoted by like numerals and in which.

DETAILED DESCRIPTION OF THE DRAWINGS

Figure 1:
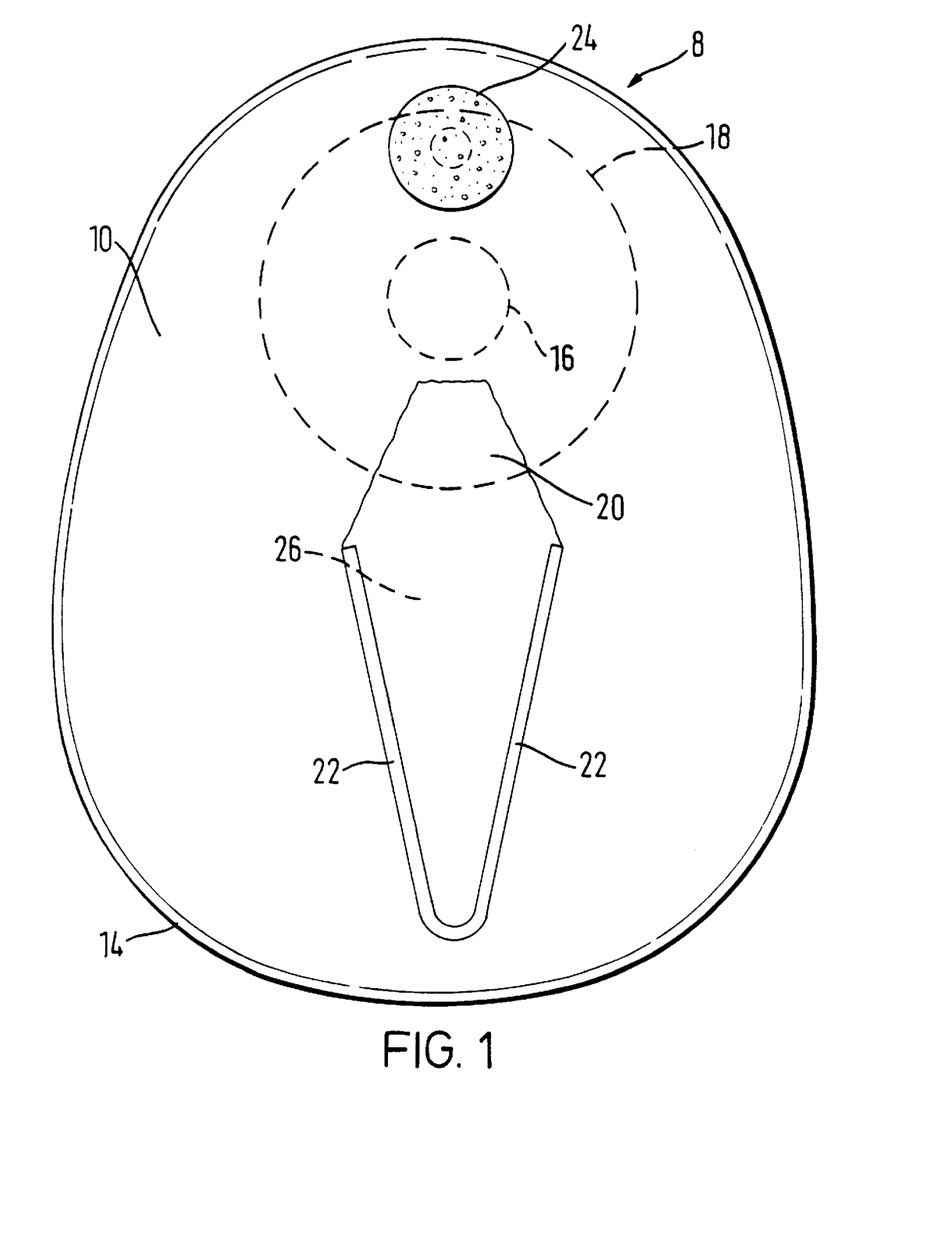
FIG. 1 is a front view of a first example of pouch according to the invention.
Figure 2:
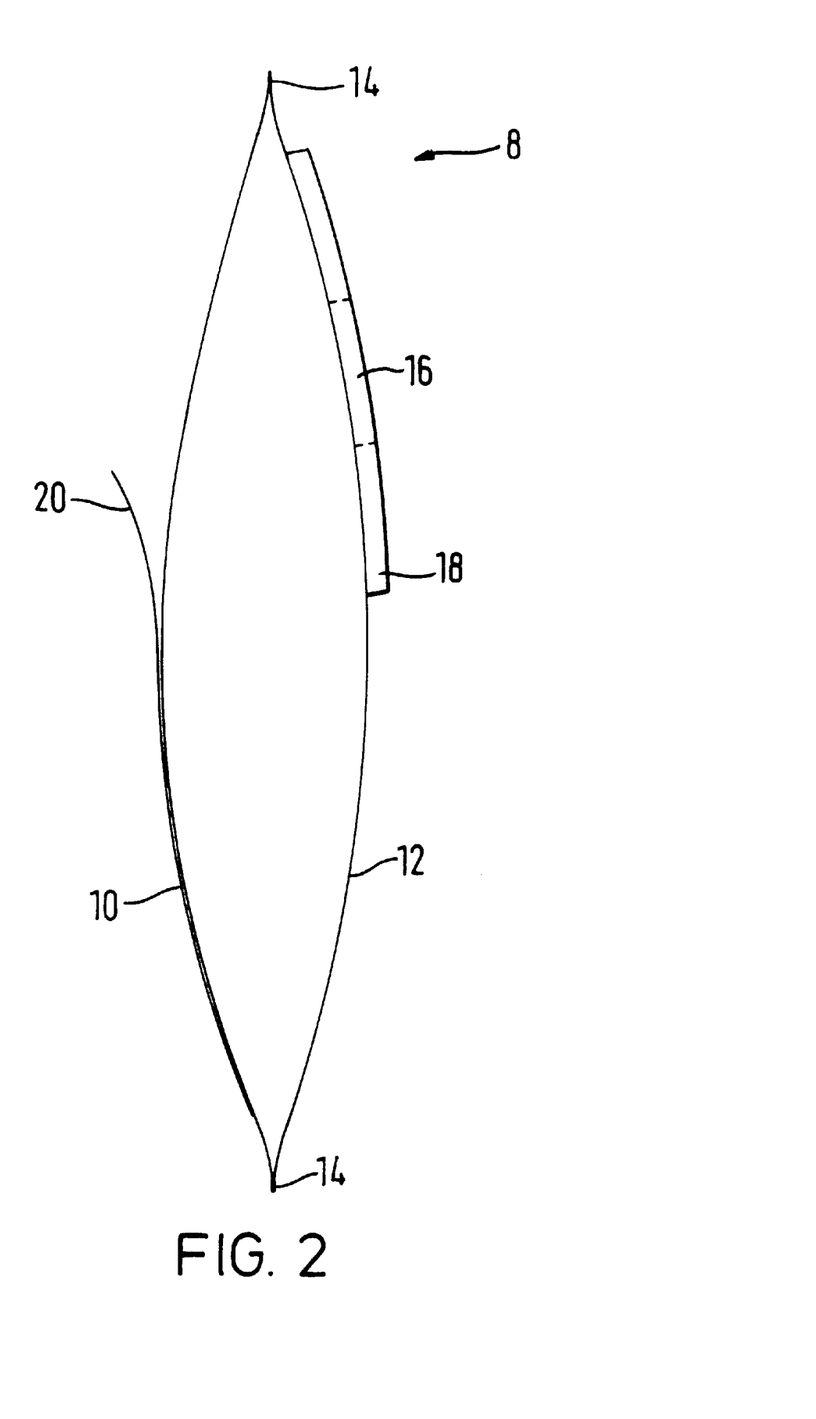
FIG. 2 is a diagrammatic cross-section through the pouch shown in FIG. 1, but not showing the filter 24 which is optional.

The pouch 8 shown in FIGS. 1 and 2 has a front wall 10 and a rear wall 12 joined by a peripheral plastics weld 14. The rear wall has a stomal orifice 16 therein and a medical grade adhesive wafer 18 surrounds this orifice. The wafer 18 enables the pouch to be realisably attached in known manner to the peristomal skin surface of the wearer. Such wafers are known and need not be further described; the reader is referred to GB 1 044 828, GB 1 088 992 and GB 1 571 657.

Referring now to FIG. 2, a tab 20, which may for example be a plastics strip, is attached to the outer surface of the wall 10 by a bar weld 22. An optional patch filter 24, e.g. of polyurethane foam or charcoal cloth, having activated carbon particles dispersed therein, is attached to an upper region of the pouch. Such filters are well known to those skilled in the art: other kinds of filter may be used provided they do not inhibit tearing away of the tab 20.

As seen in FIG. 1, the weld 22 is substantially V-shaped. It may be made by heat or RF welding. The plastics material of the tab is chosen to be compatible with the material of the pouch wall. A suitable material for the pouch wall is MF film available from W. R. Grace & Co. A suitable material for the tab 20 is also MF film, which may if desired be clear or a different colour from the pouch wall to aid identification.

The weld 22 around the tab 20 defines a flap area 26 underneath the tab 20 which remains intact with the remainder of the pouch wall in normal use, thereby preserving the integrity of the pouch, but which can be released by pulling away the tab 20.

Figure 3:
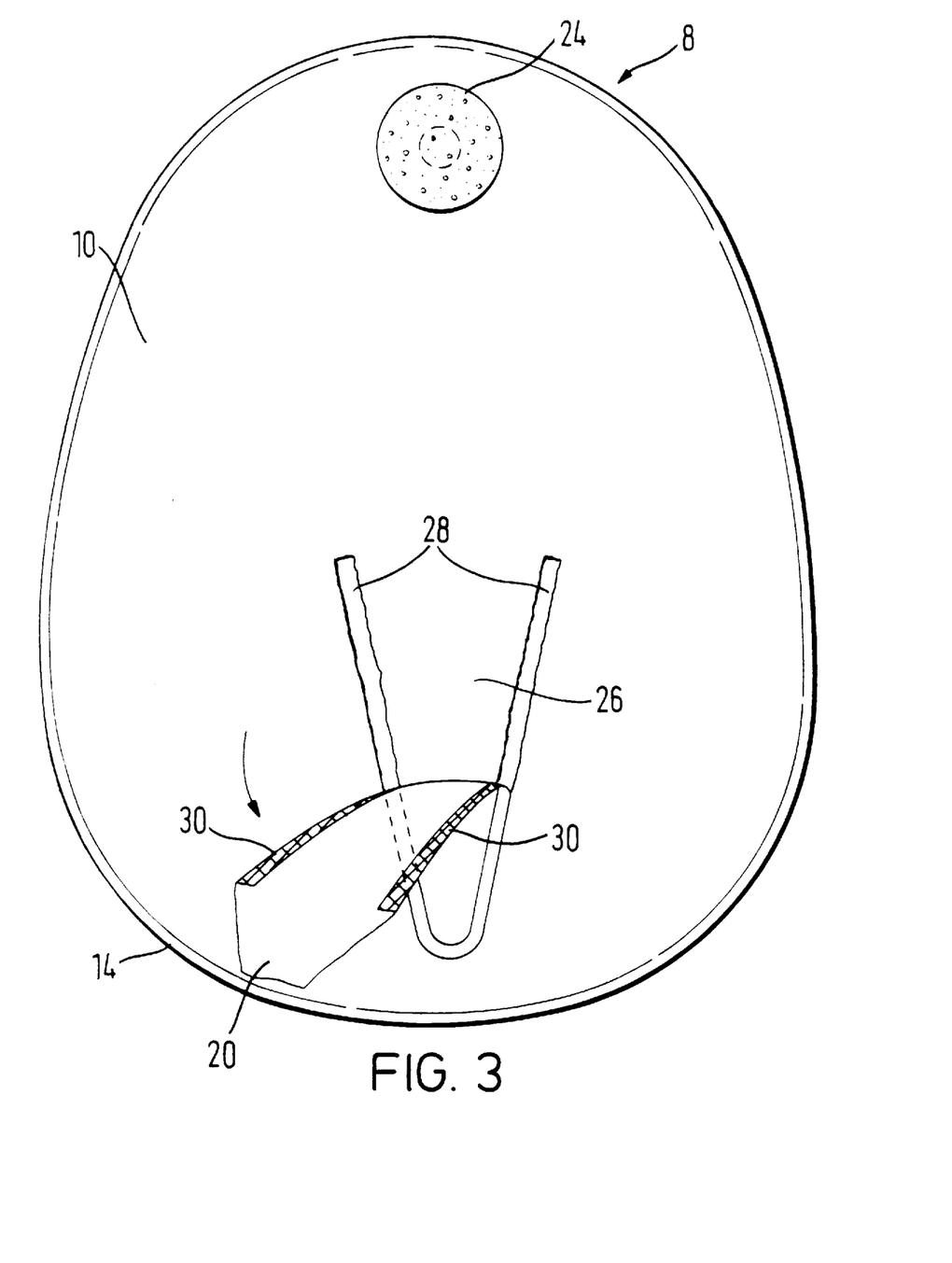
FIG. 3 is a front view similar to FIG. 1, but showing the tab partly removed.
Figure 4:
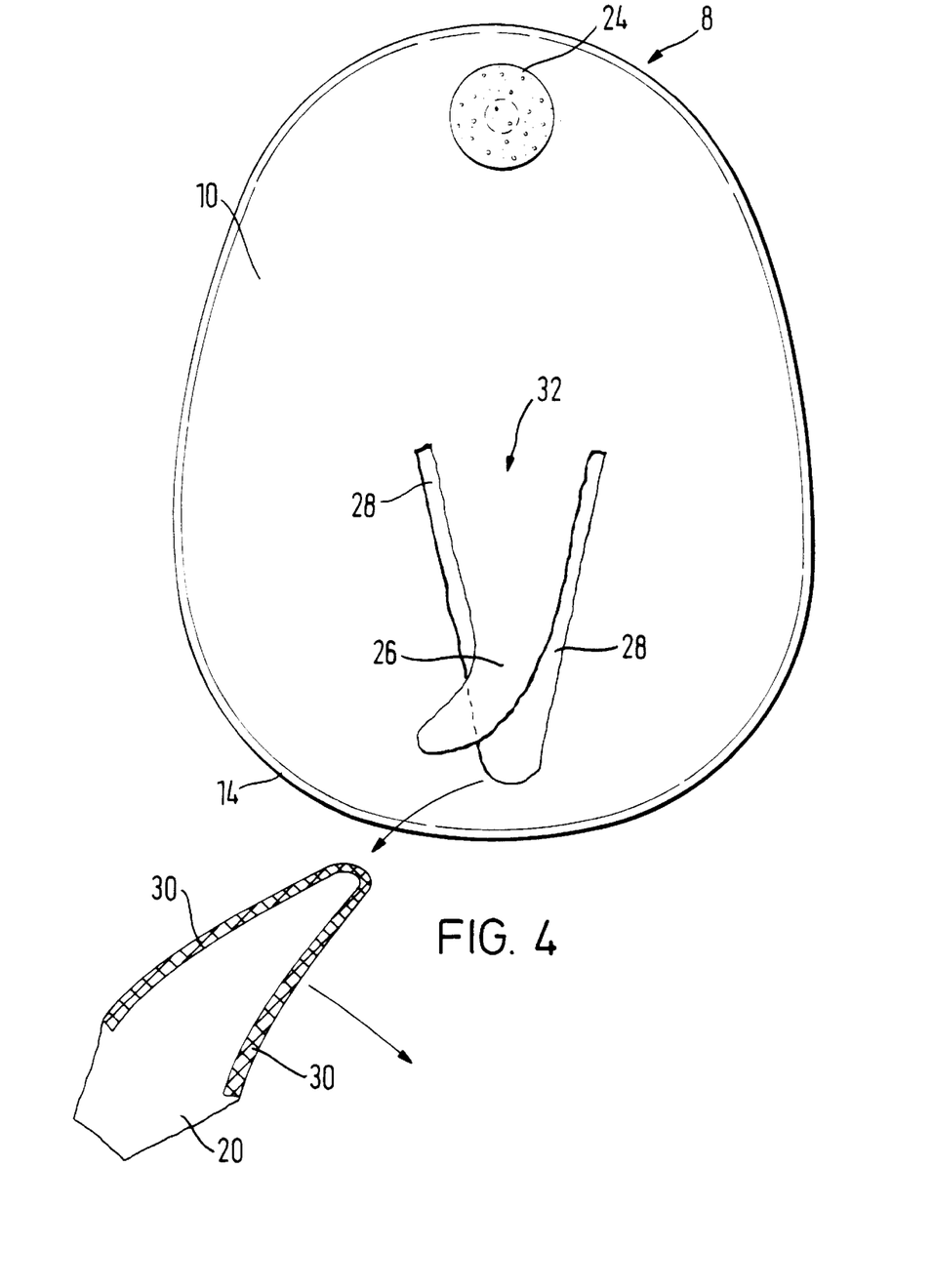
FIG. 4 is a front view similar to FIG. 3, but showing the tab completely removed.

Referring to FIGS. 1 and 3, when a wearer has finished with a pouch and wishes to dispose of it down a WC, the wearer grips the uppermost edge of the tab 20, and pulls it downwardly to tear away the tab 20. As the tab 20 is torn away, the material of the pouch wall tears along either side of the weld creating gaps 28 (FIG. 3). The pouch material welded to the tab 20 is thus torn out of the pouch wall, and remains attached to the tab (shown by numeral 30 in FIGS. 3 and 4).

Once the tab 20 has been completely torn away, the gaps 28 on either side of the flap area join up to form a V-shape (FIG. 4), and thereby release the flap area 26 from the surrounding material. The flap area 26 remains intact with the wall along the flap's uppermost edge 32, but is free to fold outwardly to allow any trapped air or other gas to escape from the pouch.

In the present embodiment, the tears occur in the pouch wall on either side of the weld, because lines (or regions) of weakness are created on either side of the welds 22 during the welding operation. As explained hereinbefore, it is believed that the lines of weakness are created by a combination of a HAZ and material thinning. The lines of weakness ensure that the tears follow the welds as the tab 20 is pulled downwardly.

It will be appreciated that the lines (or regions) of weakness will be created in the tab material as well as in the pouch material. However, the arrangement can be engineered such that the pouch material has less resistance to tearing, and will therefore always tear first before the tab begins to tear. For example, the materials used for the pouch and tab may be selected such that the tab material is a stronger type of material than the pouch material. Alternatively (or additionally), the pouch and tab may be made of materials of different thickness, to provide the tab with the greater strength. In the present embodiment, the pouch and tab are made of the same types of material (e.g. MF film), the tab material being slightly thicker than the pouch material. Typically, the pouch material may be of the order of 75 microns thick, and the tab material of the order of 100 microns thick.

It will also be appreciated that, in this example, the flap area 26 is not fully released until after the tab 20 has been pulled fully away, and the tears in the walls of the pouch have joined at the foot of the V-shape. This ensures that, while the user's fingers are possibly close to the pouch wall (holding the tab), there is very little risk of any of the pouch contents accidentally escaping from the pouch. The flap is only able to fold fully open (and thus possibly allow the escape of some of the pouch contents) when the tab has been torn off, and the user's fingers will then be clear of the pouch itself.

The provision of the flap area 26 in the opposite wall of the pouch to the stomal orifice 16 means that the gas can escape through either wall. For example, if the pouch tends to float in the WC with the front wall 10 uppermost, any gas in the pouch can escape through the opening around the flap 26. If the pouch tends to float in the WC with the rear wall 12 uppermost, gas can escape through the stomal orifice 16.

Figure 5:
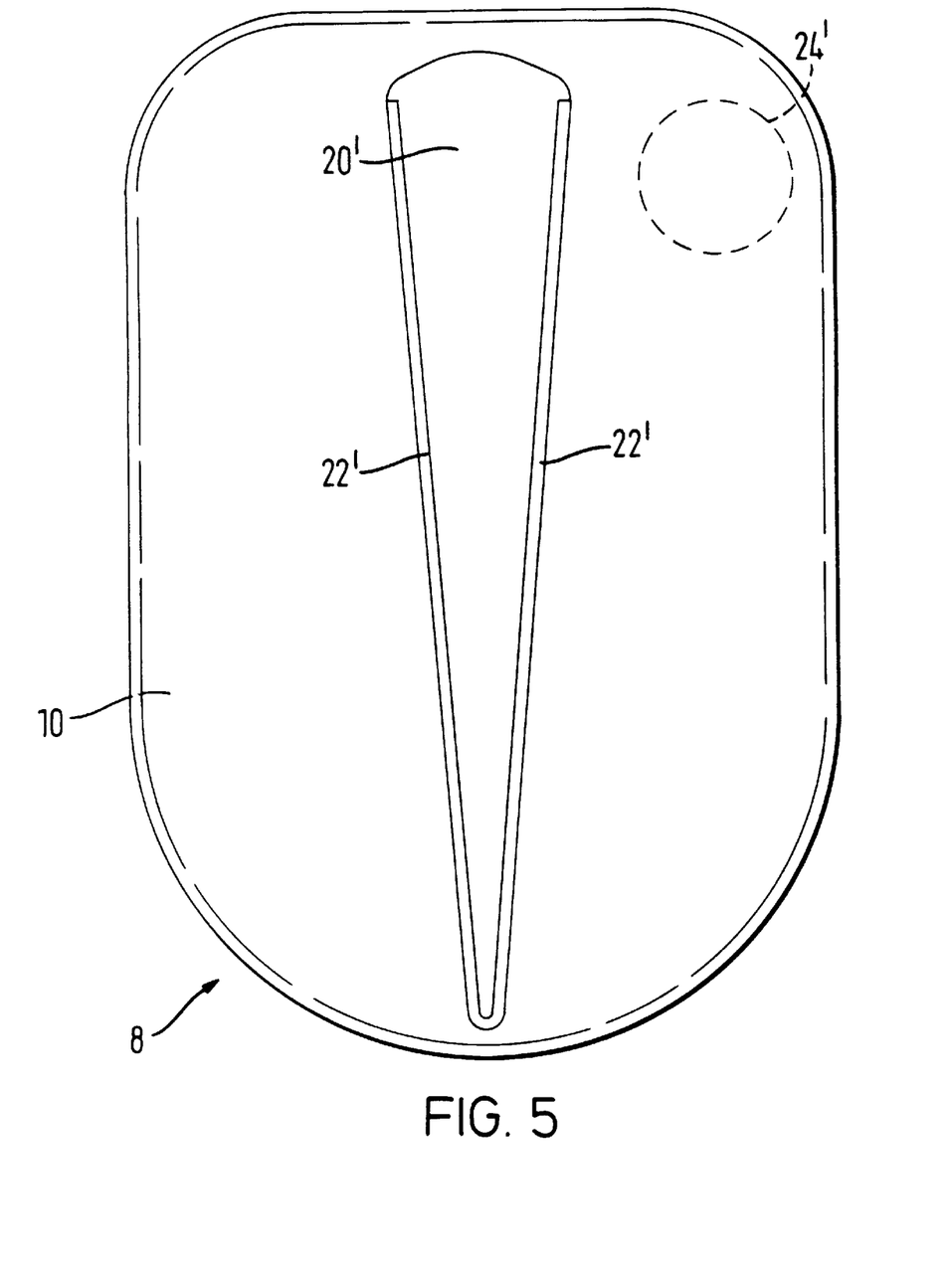
FIG. 5 is a front view of a second example of pouch.

FIG. 5 shows a second example of pouch which functionally is very similar to the first example. In the second example, the tab 20' extends substantially from the top edge of the pouch to the bottom edge, thereby defining a much larger flap area 26' in the front wall 10 of the pouch than in the first example.

When the tab 20' is pulled away, the front wall 10 will have an aperture which extends the entire length (height) of the pouch 8. This can allow the gas to escape even if the pouch is tilted at an angle in a WC. It will be appreciated that with the pouch in the first example, it may be possible for air to be trapped in a corner of the pouch if the pouch is floating at an angle with both the flap opening in the front wall 10 and the stomal orifice in the rear wall 12 below the surface of the water in the WC. Such trapped air may, in some cases still hinder flushing of the pouch down the WC waste pipe. However, by creating an aperture in at least one wall, extending from the top to the bottom of the pouch, the chances of this occurring are significantly reduced.

As illustrated by the broken line 24' in FIG. 5, the filter (if fitted) may be positioned in the pouch wall 10 to one side of the tab 20', so as not to interfere with the tab.

While a V-shaped weld is currently preferred, the tab could be welded to one pouch wall by two parallel bar welds, one running down each side of the tab. Of course in that event the remainder of the tab would be free of attachment to the pouch wall. In this embodiment of the invention, the tab may be rectangular and its width is desirably wide enough for a finger or thumb to be inserted behind it (that is, between tab and adjacent pouch wall) by the wearer of the pouch, so that the tab can be torn off so causing two tears in the pouch wall. Tearing the tab off in this way ensures that the pouch is itself sufficiently torn that it can be satisfactorily disposed of in a WC.

As a yet further possibility, the weld 22 could extend entirely around an area of the pouch wall, and thus define a hatch area in the wall. Upon pulling the tab away, the tab would tear out the entire hatch area of the wall, leaving an aperture for the escape of trapped gas. The hatch area would probably then remain attached to the tab upon removal.

Figure 6:
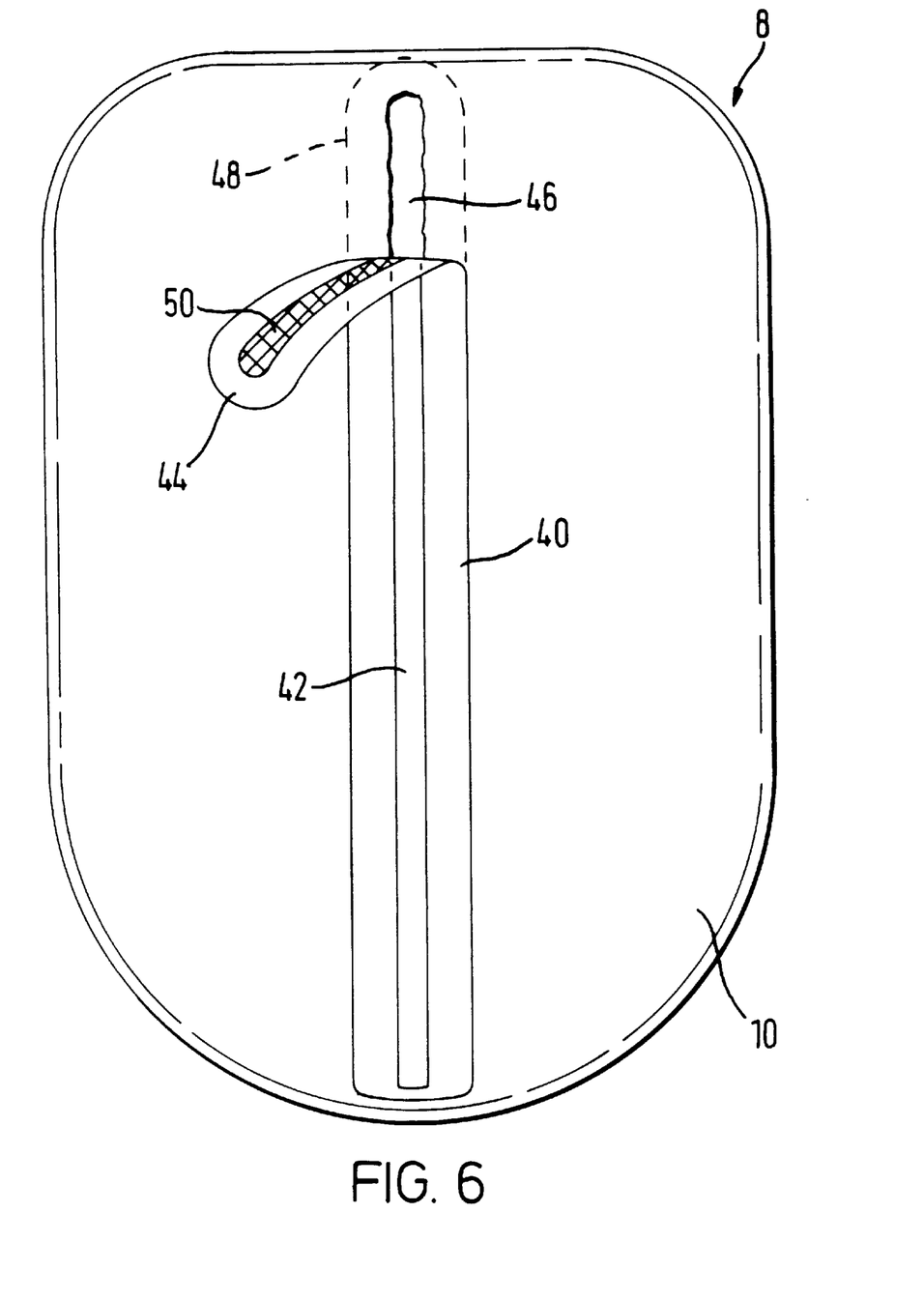
FIG. 6 is a front view of a third example of pouch, showing a strip partly pulled.

A yet further example of pouch is illustrated in FIG. 6. In this example, the tab, in the form of a longitudinal strip 40 is secured to the pouch wall 10 by a single bar weld 42 extending in a straight line from the top edge of the pouch to the bottom edge. The strip 40 has a free, non-welded upper end 44 by which the strip 40 can be grasped, and pulled downwardly in the same manner as the tabs of the earlier examples. In FIG. 6, the dotted line 48 represents the position of the strip 40 in its normal welded position.

Upon pulling the strip 40 downwardly as shown in FIG. 6, a tear 46 is created in the pouch wall 10. In the same manner as that described previously, material 50 in the region of the weld is torn out of the pouch wall creating a gap through which any gas trapped in the pouch can escape during disposal down a WC. Thus, instead of tearing a round a flap as in the earlier examples, an opening is created simply by tearing out the material 50 to which the strip 40 is welded.

In the example illustrated in FIG. 6, the weld 42 is relatively narrow, and is not significantly wider than the welds 22 in the earlier embodiments. However, the weld 42 could be wider than that shown, and thus create a wider opening when the strip 44 is torn away.

It will be appreciated that, in the above examples in general, the width of the individual weld does not affect the pulling force which a user has to apply to tear away the tab or strip. This is because the tearing action is a result of the pouch material tearing and not destruction of the weld itself.

In the above examples the tab is completely separated from the pouch when the tab is pulled away. This provides a positive indication to the user that the tearing has been completed, and can keep the user's hands clear of the opening formed in the pouch wall in case any of the pouch contents escape before the pouch is dropped into the WC. However, if desired, the tab could also be designed to remain attached to the pouch, for example along a bottom edge, so that the tab and the pouch will always be disposed of hygienically together down the WC.

In the above examples either oriented or non-orientated plastics material may be used for the pouch and the tab. Orientation creates a natural weakness in the material to tearing parallel to the or a direction of orientation. In the first and second examples in which two tears are created, extending in slightly different directions, it is expected that non-orientated plastics material may provide better results. The tearing would then only occur along the lines of weakness on either side of the welds. In the third example, orientated material may be used, with the weld 42 aligned parallel to the or a direction of orientation.

Any suitable plastics material may be used for the pouch and tab. In general, the material is likely to be a laminate of different layers arranged as a film. For example, the MF film referred to above is a laminate which has surface layers of an ethylene vinyl acetate (EVA) material. If the tab is to be welded to the pouch wall, the pouch and tab have to be or include compatible material or materials for welding. Suitable plastics materials include (but are not limited exclusively to) polyolefins and copolymers, of which EVA is an example, and polyamides and copolymers, for example, a polyesteramide.

Welding is a preferred method for securing the tab to the pouch wall, since welding is typically used extensively in the production of the pouch. In particular, the pouch is normally welded around its periphery (or part of the periphery if the pouch is formed from a single sheet). The welding of the tab to the pouch wall would typically be carried out prior to welding around the periphery, to ensure that the pouch walls are not accidentally welded together along the welds 22 or 42 in the examples.

Figure 7:
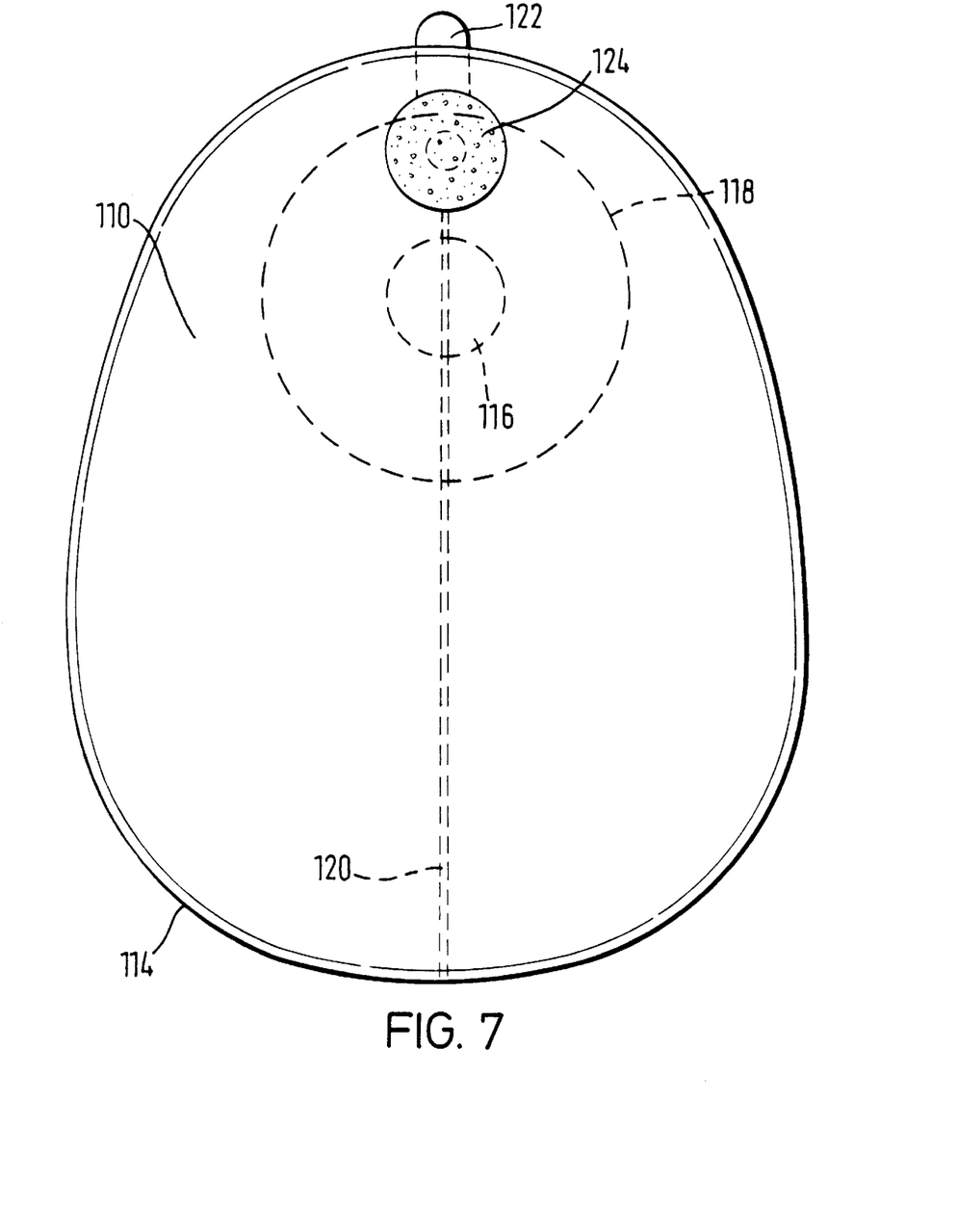
FIG. 7 is a front view of a fourth example of pouch according to the invention.
Figure 8:
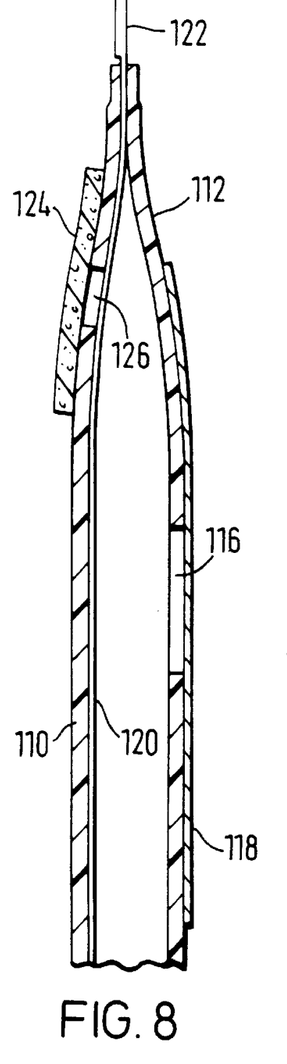
FIG. 8 is a diagrammatic cross-section through an upper part of the pouch shown in FIG. 7.

Referring now to FIGS. 7 and 8, the pouch 108 has a front wall 110 and a rear wall 112 joined by a peripheral plastics weld 114. The rear wall has a stomal orifice 116 therein and an adhesive wafer 118 surrounds this orifice. The wafer 118 enables the pouch to be realisably attached in known manner to the peristomal skin surface of the wearer.

Referring now to FIG. 8, a tear strip or filament 120, which may for example be a filament of polyester, is attached to the inner surface of the wall 110 and passes between the walls 10 and 112 where they are joined at the top of the pouch. The filament 120 has one end attached to a tab 122. It is arranged parallel to the direction of orientation of the plastics material forming the wall 110. A patch filter 124, e.g. of polyurethane foam or particularly charcoal cloth, or other non-woven filter substrate, and having activated carbon particles dispersed therein, is attached to an upper region of the pouch. Such filters are well known to those skilled in the art; other kinds of filter may be used provided they do not inhibit tearing away of the tear strip 120. A hole 126 in the pouch wall 110 permits flatus gases to reach the filter 124. In use, the tab 122 is grasped and pulled with the pouch held over the WC. This completely "unzips" the wall 110 of the pouch, that is to say, a tear is made along the length of the pouch wall. The pouch can then be flushed away without difficulty.

Figure 9:
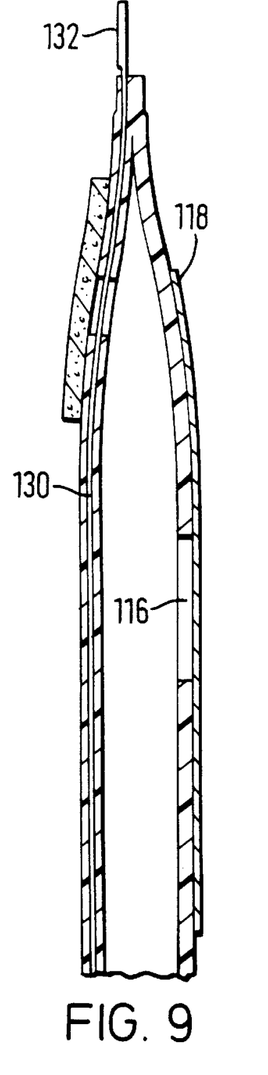
FIG. 9 is a cross section similar to FIG. 8 but showing a fifth embodiment of the invention.

The embodiment of the invention shown in FIG. 9 has a tear strip 130, which may be a polyester filament, embedded within the material of the wall 110. The tear strip 130 extends beyond the wall 110 and has a grip tab 132 attached at its upper end. When the tab 132 of the filament 130 is pulled (towards the left and downwardly as seen in FIG. 3) the filament is stripped out of the wall 110. This weakens the wall to such an extent that a vertical tear or split in the wall 110 occurs.

Figure 10:
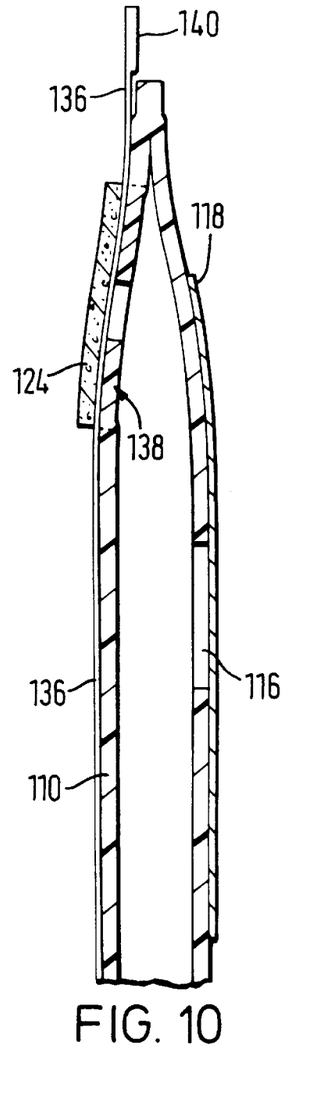
FIG. 10 is a cross section similar to FIG. 8 but showing a sixth embodiment of the invention.

A further embodiment of the invention is shown in FIG. 10, in which a tear strip 136 is located on the outside surface of the wall 110 and passes under the filter 124. The tear strip 136 is welded through to the area denoted 138 of the pouch, prior to attachment of the filter 124. The filter may be attached to the wall 110 with adhesive. A tab 140 enables a protruding part of the filament to be gripped by finger and thumb. As the filament is stripped away, a section of the pouch wall 110 is in effect torn in half, and the tear is propagated along the major portion of the pouch wall. The pouch may then be disposed of down a WC without difficulty.

Figure 11:
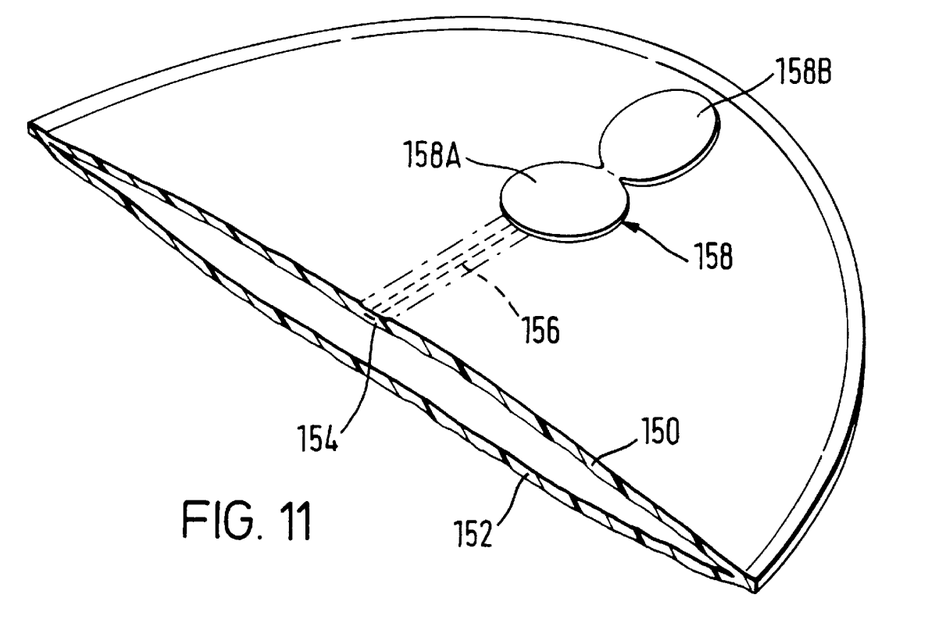
FIG. 11 is a partly cut-away isometric view of an upper part of a WC-disposable pouch according to a further embodiment of the invention.

Referring now to FIG. 11, an isometric view, partly cut away, of an upper part of a WC-disposable pouch according to a further embodiment of the invention is shown. The pouch has a front wall 150 and a rear wall 152 and has a linear heat-affected zone 154 extending linearly along the length of the pouch. Of course, while a linear HAZ is illustrated, there is no reason why a non-linear HAZ should not be employed instead. A polyester filament 156 is attached to the outer surface of the wall 150 e.g. by heat welding or adhesive, and has one end securely attached to a deodorizing filter 158. The filter 158 has a portion 158A attached to the pouch wall and a portion 158B which is free of the pouch wall. As will be understood, the pouch wall 150 has one or more holes therein adjacent to the filter so that flatus gases can exit the pouch via the filter 158. It is preferable that the filament should run parallel to the direction of the HAZ. The filament should run along or closely adjacent to the HAZ. In use, by gripping and lifting and pulling the filter tab 158B the filament 156 may be stripped out of the wall 150 leaving a substantial tear therein. Once torn in this way, the pouch may be disposed of down a WC without difficulty.

Figure 12:
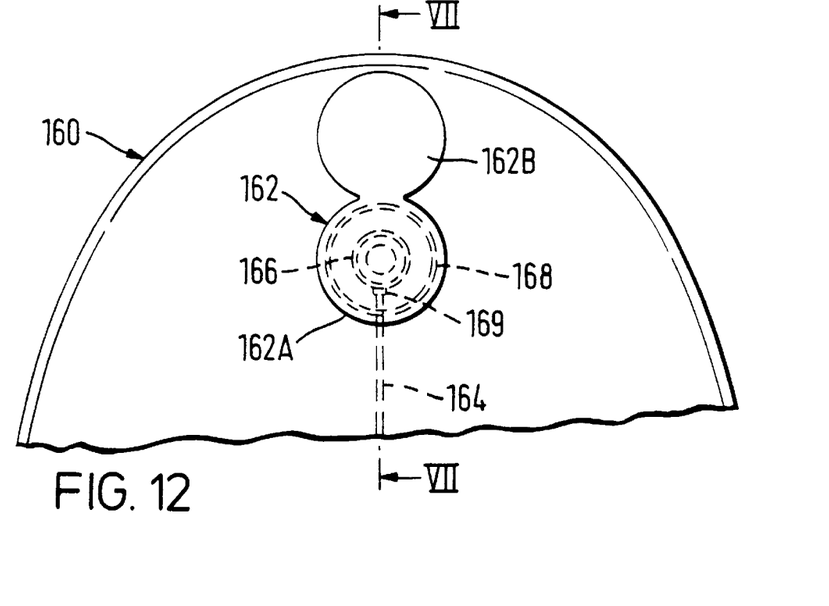
FIG. 12 is a similar view to FIG. 11 and illustrates a pouch having a "figure of 8" filter attached thereto.
Figure 13:
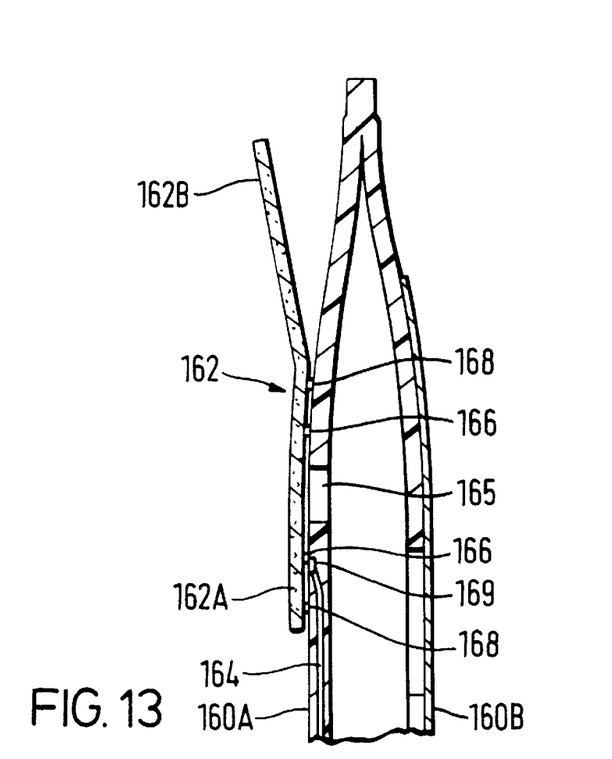
FIG. 13 is a cross-section in a vertical plane of the upper part of the pouch shown in FIG. 12.

In FIGS. 12 and 13, further detail is given of one preferred arrangement whose basic features are similar to FIG. 11. FIG. 12 shows the front view of an upper portion of a pouch 160 to which is attached a "figure of 8" shaped filter 162. The pouch has walls 160A, 160B. FIG. 13 is a cross section on the plane VII—VII of FIG. 12 showing the filter portion 162A and the tab portion 162B of the filter 162, which preferably is die cut from carbon cloth type filter media. A hole 165 in the pouch wall 160A permits flatus gases to reach the filter 162. A tear filament 164 (preferably a polyester filament) is joined e.g. by an annular ring weld 166 to the filter portion 162A. An annular intermittent ring weld 168 is located roughly concentric with, and to surround, the weld 166. At 169, there is seen a unitary joint at which an end of the filament is attached, e.g. by welding to the filter portion 162A.

In use, the user holds the upper portion of the pouch 160 with one hand, and grips the tab 162B with finger and thumb of the other hand. The tab 162B is pulled downwardly firmly, which destroys the annular ring weld where it is attached to the pouch wall and also breaks the intermittent weld 168; however the joint of the filter part 162A to the filament 164 is made sufficiently strong that this connection is not broken. Continued downward pulling tears the pouch wall 160A. The pouch can then be readily disposed of down a WC. The filament 164 may be attached to an external surface of the pouch wall 160A or may be embedded in said wall.

As mentioned, it is preferred to manufacture the pouch filter as a "figure of 8", but only weld one of the two circular parts to the pouch film with the remaining half of the '8' forming the basis of the tab, i.e. half of the filter material is effectively redundant from the filtering point of view but creates the tab to enable tear initiation. The filament is securely bonded to the filter area and will tear away with the filter once this process has been initiated.

In the above description, reference has been made to embedding the filament within one of the pouch walls. One convenient way to achieve this is to place the filament between two thin films which are then laminated together so that the major length of the filament is fixedly maintained between them.

To the best of the Applicants' present knowledge and belief, in the welding of the polyester filament to the pouch film, the heat will create a line of orientation in the proximity of the filament and with ultimate tear initiation, a tear will run down this line proximal to the filament. It is well known in the welding of metals that fracture nearly always takes place next to the actual weld and rarely within the weld material itself. A combination of polymer thinning and molecular orientation next to the filament is considered sufficient to allow rupture of the pouch film as required. Polymer thinning as well as or instead of molecular orientation next to the heat welded zone can be employed to ensure that a thinner area will tear first.

Modifications may be made without departing from the invention; for example the tab could be secured to the pouch wall by two strips of strongly adhesive material, in which event the tab would be made of a material having a tensile strength greater than that of the pouch wall.

While features believed to be of particular importance have been identified in the above description and the appended claims, the Applicant claims protection for any novel feature or combination of features described herein and/or illustrated in the accompanying drawings, irrespective of whether emphasis has been placed thereon.

What is claimed is:

1. A water closet disposable ostomy pouch comprising:
   inner and outer pouch walls of plastic material, said pouch walls being welded together along a peripheral edge to form a pouch; and
   a tab attached to one of said pouch walls, said tab including a finger-grippable, pullable, free end portion and a plastic material portion attached to said free end portion,
   said plastic material portion being welded to said pouch wall by a weld, said plastic material portion being tearable from said pouch wall proximate to said wall upon pulling of said free end portion so as to create an opening in said pouch wall for facilitating disposability of the pouch.

2. The water closet disposable ostomy pouch of claim 1 wherein said weld includes a weakened heat affected zone in said pouch wall.

3. The water closet disposable ostomy pouch of claim 2 wherein said pouch wall has an area of weakness adjacent to said weld.

4. The water closet disposable ostomy pouch of claim 2 wherein said weld has an outer surface on said pouch wall and said free end portion is attached to said outer surface of said weld.

5. The water closet disposable ostomy pouch of claim 1 wherein said weld extends partly around an area of said pouch wall so as to define a flap.

6. The water closet disposable ostomy pouch of claim 5 wherein said flap has a v-shape.

7. The water closet disposable ostomy pouch of claim 1 wherein said weld extends entirely around an area of said pouch wall.

8. The water closet disposable ostomy pouch of claim 1 wherein said pouch wall includes a relatively thin region proximate to said weld.

9. The water closet disposable ostomy pouch of claim 1 wherein said free end portion and pouch wall are composed of the same material and the said free end portion is thicker than said pouch wall.

10. The water closet disposable ostomy pouch of claim 1 wherein the pouch wall has a filter member attached thereto and said free end portion includes said filter member.

11. The water closet disposable ostomy pouch of claim 1 wherein said plastic material portion is fully tearable from said pouch wall by pulling said free end portion.

12. The water closet disposable ostomy pouch of claim 1 wherein said plastic material portion is partially tearable from said pouch wall by pulling said free end portion.

13. The water closet disposable ostomy pouch of claim 1 wherein said weld includes two separate weld portions in said pouch wall.

14. The water closet disposable ostomy pouch of claim 1 wherein said free end portion is welded to said pouch wall so as to permit a finger to be placed between said tab portion and said pouch wall.

15. The water closet disposable ostomy pouch of claim 1 wherein said pouch wall is composed of a linearly oriented plastic and said plastic material portion is tearable parallel to the linear orientation of said linearly oriented plastic.

* * * * *